United States Patent
Machado

(10) Patent No.: US 10,058,017 B1
(45) Date of Patent: *Aug. 21, 2018

(54) ELECTROMAGNETIC CONTAMINATION NEUTRALIZATION COMPOSITION, DEVICE, AND METHOD

(71) Applicant: Jose Machado, Miami, FL (US)

(72) Inventor: Jose Machado, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/783,073

(22) Filed: Oct. 13, 2017

Related U.S. Application Data

(63) Continuation of application No. 15/080,227, filed on Mar. 24, 2016, now Pat. No. 9,820,418.

(51) Int. Cl.
*H05K 9/00* (2006.01)

(52) U.S. Cl.
CPC ......... *H05K 9/0083* (2013.01); *H05K 9/0088* (2013.01)

(58) Field of Classification Search
CPC ........................... H05K 9/0083; H05K 9/0098
USPC .................................................. 174/388, 394
See application file for complete search history.

(56) References Cited

U.S. PATENT DOCUMENTS

| | | | | | |
|---|---|---|---|---|---|
| 5,366,795 | A | * | 11/1994 | Goto | G11B 5/716 428/212 |
| 5,698,839 | A | * | 12/1997 | Jagielinski | G06K 19/06196 235/449 |
| 2006/0083948 | A1 | * | 4/2006 | Kawaguchi | H01F 10/08 428/692.1 |

* cited by examiner

*Primary Examiner* — Sherman Ng
(74) *Attorney, Agent, or Firm* — Sanchelima & Associates, P.A.; Christian Sanchelima; Jesus Sanchelima

(57) ABSTRACT

A tangible device such as a credit card shaped device that includes at least one waffler carved therein. A bottom stabilizing material in the shape of a film or sheet is placed within the waffler. A nano-scaled metal in powdered form that is ferromagnetic in nanoscale, such as gold, is then added above the bottom stabilizing film. A ferromagnetic powder in nanoscale is added to the nano-scaled metal and a top stabilizing film is placed thereon. Ceramic powder is then used to further stabilize the composition and finally all the components are sealed within the waffler. The nano-scaled metals can be affixed to the stabilizing films using atomic layer deposition. The present invention is used to neutralize the electromagnetic contamination emitted from a plurality of electronic devices by organizing the polarity of the spin of the element particles within their radiation.

8 Claims, 5 Drawing Sheets

US 10,058,017 B1

ELECTROMAGNETIC CONTAMINATION NEUTRALIZATION COMPOSITION, DEVICE, AND METHOD

1. OTHER RELATED APPLICATIONS

The present application is a continuation application of pending of U.S. patent application Ser. No. 15/080,227 filed on Mar. 24, 2016, which is hereby incorporated by reference.

BACKGROUND OF THE INVENTION

2. Field of the Invention

The present invention relates to a composition, method and a device that neutralizes the effects of electromagnetic contamination in a given area and more particularly to a device that neutralizes the harmful effects of non-ionizing radiation from artificial sources.

3. Description of the Related Art

Several designs for devices that reduce electromagnetic contamination have been designed in the past. None of them, however, include the ability to completely neutralize the effects of electromagnetic contamination instead of just reducing their effects.

Applicant believes that a related reference corresponds to non-patent publications found on www.swiftfire.org/rid-electromagnetic-radiation related to cell phone bluetooth shields, personal body shields, house shields, and laptop/microwave shields in connection with electromagnetic contamination. These shields and similar devices known in the art are only capable of reducing but not completely neutralizing the damaging effects of electromagnetic contamination.

The present invention uses a novel and non-obvious combination of ferromagnetic material at a nanoscale to eliminate and create a harmonious arrangement of particles of electromagnetic contaminants, thereby neutralizing their harmful effects.

The neutralization is accomplished by organizing the polarization of the spin of the element particles, including electrons. Care is taken to organize the spin of the element particles without affecting their trajectory.

Other documents describing the closest subject matter provide for a number of more or less complicated features that fail to solve the problem in an efficient and economical way. None of these publications suggest the novel features of the present invention.

SUMMARY OF THE INVENTION

It is one of the main objects of the present invention to provide a device that neutralizes the effects of electromagnetic contamination in a given space.

It is another object of this invention to provide a device that reduces the presence of static, both magnetic or electric, thereby conserving the life span of electronic equipment and preventing electrical shock exposures to humans and animals.

It is still another object of the present invention to provide a device that optimizes the consumption of electricity.

It is another object of this invention to provide a device that includes a composition that can be adjusted to cooperate with a plurality of devices depending on the required use.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
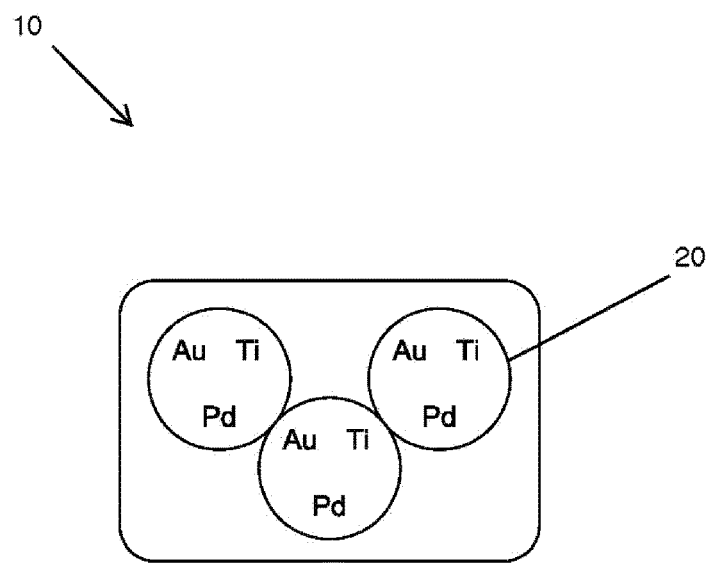
FIG. 1 represents a top plan view of the present invention wherein three wafflers 20 are created in the device and uniformly filled with the ferromagnetic composition subject of the present invention.
Figure 2:
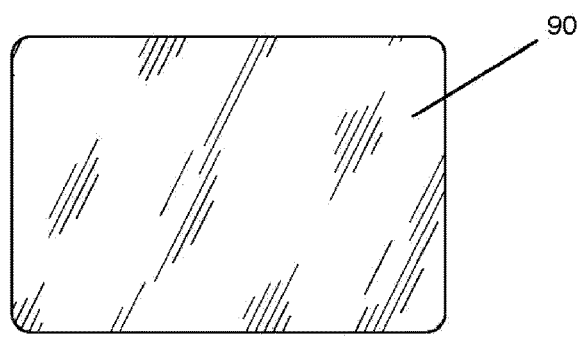
FIG. 2 shows a top plan view of the present invention wherein the filled wafflers 20 of FIG. 1 have been sealed using a laminating material 90.

Referring now to the drawings, where the present invention is generally referred to with numeral 10, it can be observed that it basically includes a composition comprising metals in nano-scale 40;50 that when combined with stabilizing materials 30;70 such as titanium, ceramic powder, palladium or similar materials creates a composition with ferromagnetically stable properties. The metals used in nano-scale 40;50 that are combined with the stabilizing materials 30;70 include gold, palladium, and titanium in powder form.

The stabilizing materials 30;70 can further include in the form of films/sheets: an aluminum/lithium combination with reinforced silicon carbide; a high-density polyethalyne; a polypropelyne, a polycarbonate; or a quartz. The present invention includes two sheets of a stabilizing material 30;70 parallel and spaced apart with respect to each other using a predetermined amount of the above metals in nano-scale.

The method to create the present invention includes indenting a predetermined amount of wafflers 20 into a tangible device. A bottom sheet 30 of stabilizing material, such as titanium, is then positioned within one or more of the wafflers 20. One of the nano-scaled metals in powdered form 40, such as titanium, can be spread across the bottom sheet 30. A second nano-scaled metal in powdered form 50, such as gold, can be mixed in with the first nano-scaled metal 40. A ferromagnetic powder 60 can be similarly combined with both nano-scaled metals in powdered form 40;50 to increase the device's effectiveness. Then, a top sheet 70 of a stabilizing film is placed above the powdered metals, thereby sandwiching them therein.

Ceramic powder 80 is then spread above the top sheet 70 made of a stabilizing material. The top and bottom sheets 30;70 can be made of the same or different stabilizing material. Finally, a plastic lamination layer is used to seal in the top sheet, the nano-scaled metals in powdered form 40;50 and the bottom sheet 30 within the waffler 20 indented into the tangible device 10.

In a preferred embodiment each particle of the nano-scaled metals in powdered form 40;50 have a diameter ranging from 40-100 nanometers. The optimal diameter being 97 nanometers.

The remaining wafflers 20 are then filled in the same manner described above and the tangible device 10 is then placed adjacent to the items emitting electromagnetic contamination including non-ionizing radiation from artificial sources. In one embodiment, each waffler 20 has a substantially circular shape having a predetermined diameter. A preselected amount of the composition is uniformly spread across each waffler 20 at the ratio of 0.0009 grains for each millimeter of the waffler's surface.

Figure 3:
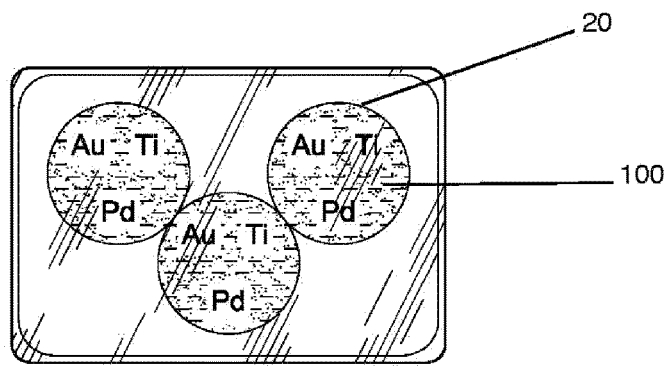
FIG. 3 illustrates an alternate embodiment wherein a molecule stabilizing additive in liquid form 100 has been added to each waffler prior to sealing.
Figure 1A:
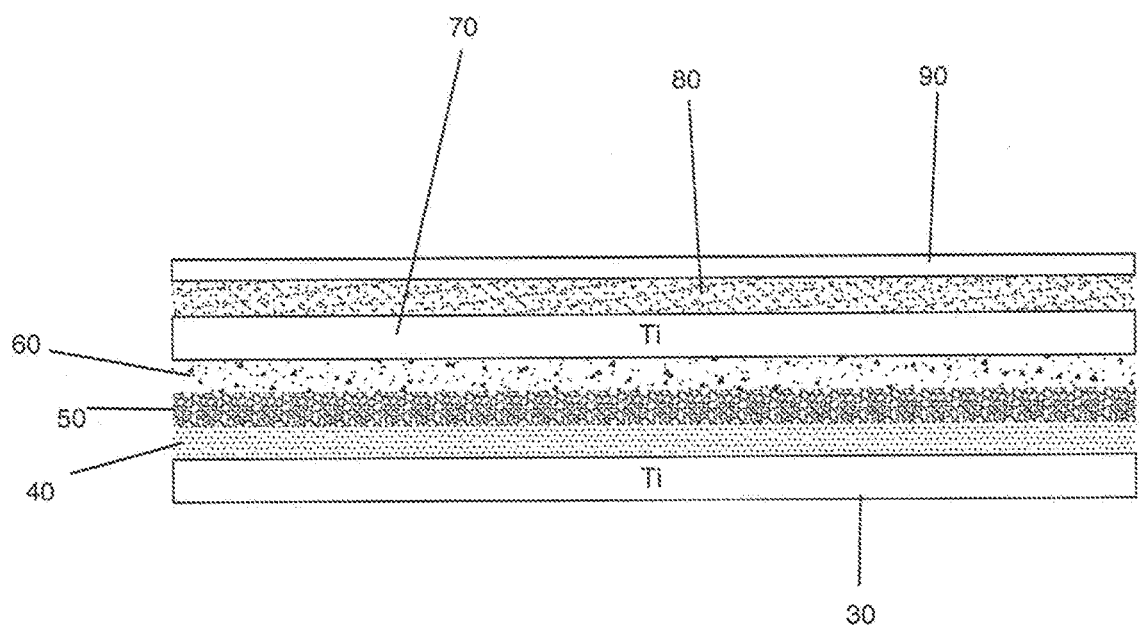
FIG. 1A shows a see-through front elevational view of the inside of a waffler showing the various components found therein.
Figure 4:
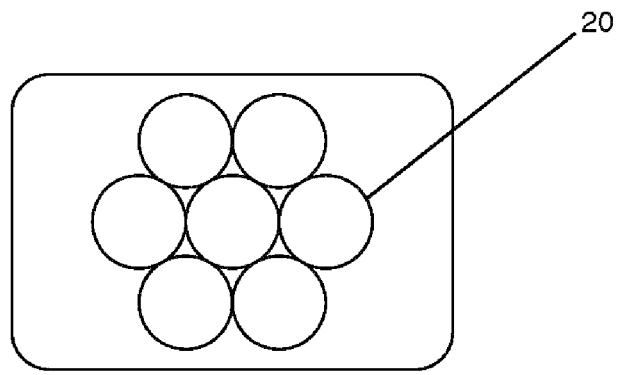
FIG. 4 is a representation of an alternate embodiment wherein additional wafflers 20 are used so that more ferromagnetic material 60 and nano-scale metals 40;50 can be added to the device to cooperate with larger uses.
Figure 5:
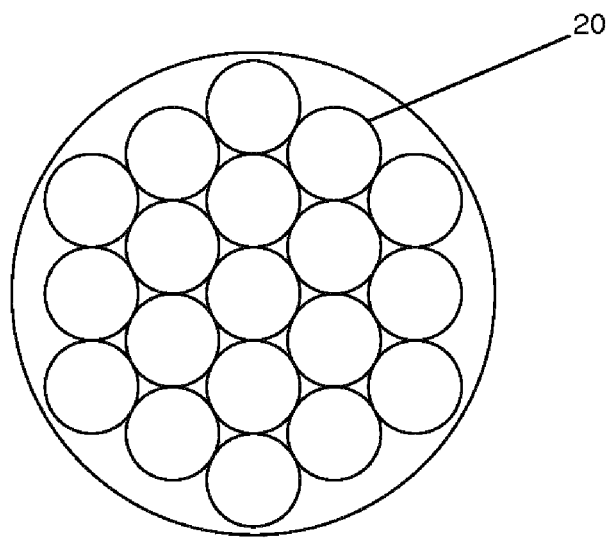
FIG. 5 is a representation of an alternate embodiment wherein additional wafflers 20 are used so that more ferromagnetic material 60 and nano-scale metals 40;50 can be added to the device to cooperate with larger uses.
Figure 6:
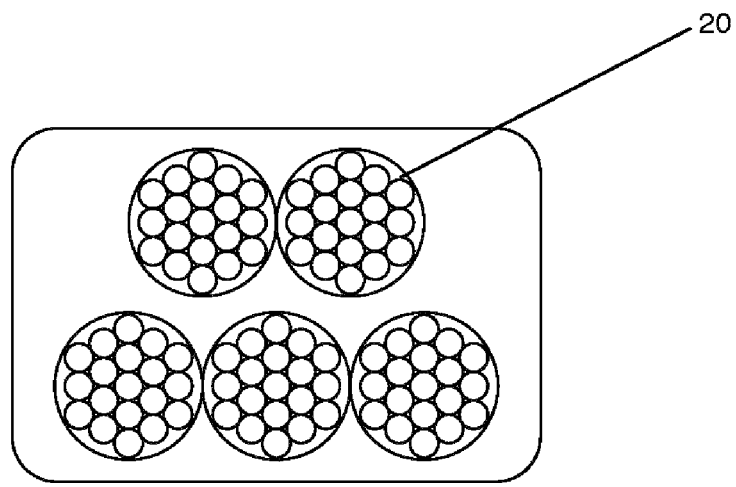
FIG. 6 is a representation of an alternate embodiment wherein additional wafflers 20 are used so that more ferromagnetic material 60 and nano-scale metals 40;50 can be added to the device to cooperate with larger uses, such as industrial applications.
Figure 7:
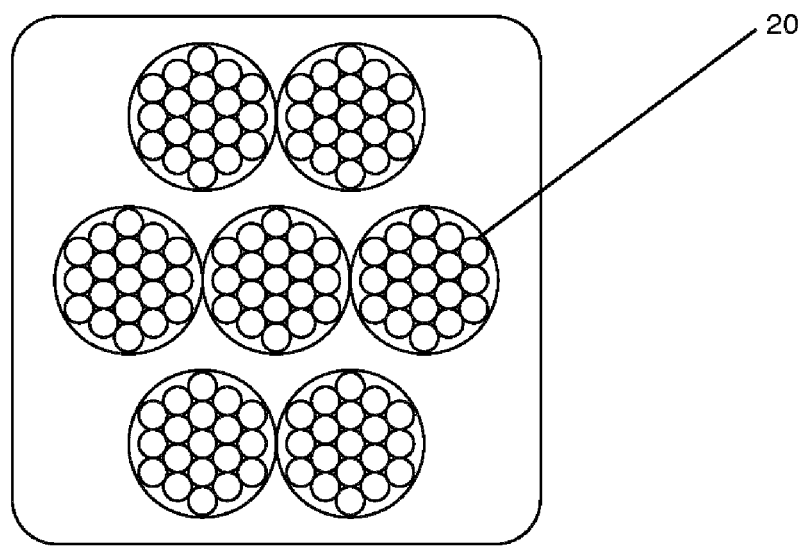
FIG. 7 is a representation of an alternate embodiment wherein additional wafflers 20 are used so that more ferromagnetic material 60 and nano-scale metals 40;50 can be added to the device to cooperate with larger uses, such as industrial applications.
Figure 8:
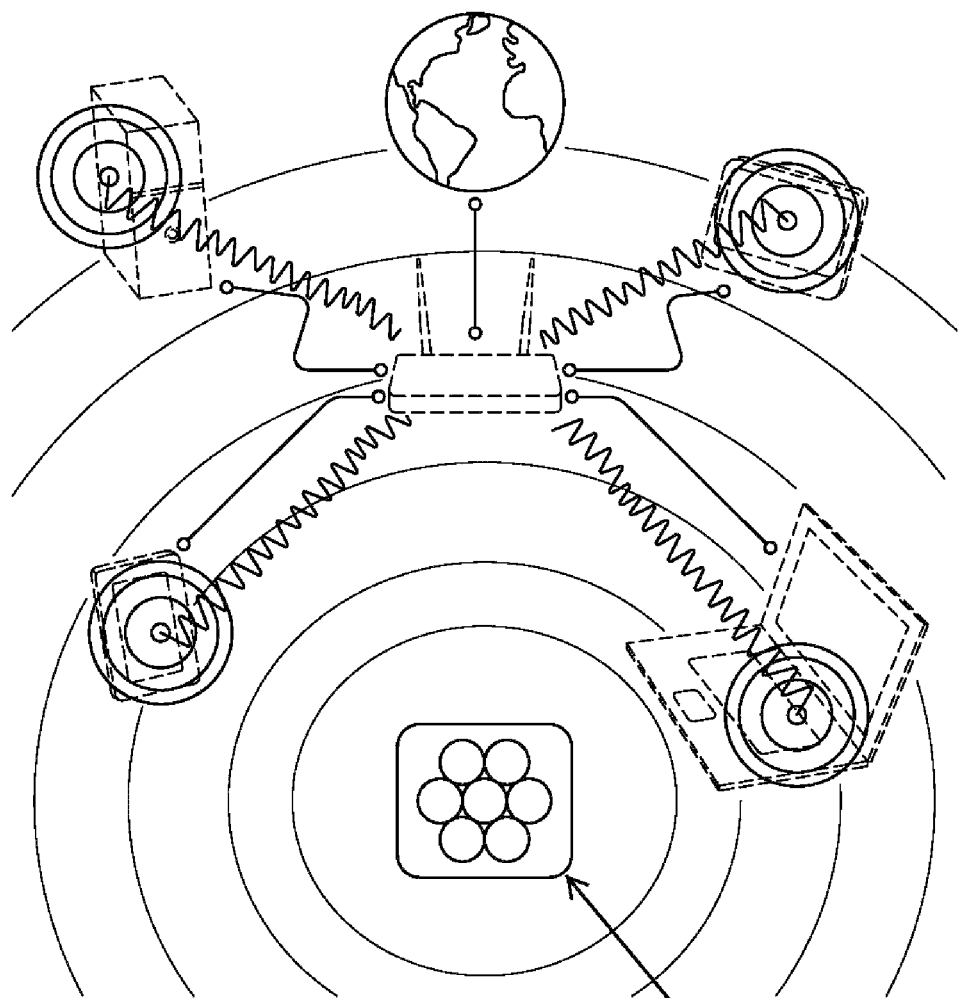
FIG. 8 shows the present invention 10 in its operating environment showing a plurality of devices that emit electromagnetic contamination.

Optionally, a molecule protecting additive in liquid form 100 is applied to each waffler 20 having the composition therein as shown in FIG. 3. The additive is comprised of alkanethiol or tetraalkyl ammonium.

The present invention requires that the nanoscale metals 40;50 used with the apparatus wafflers 20 be ferromagnetic when in nanoscale. Materials that are ferromagnetic in their original state will not work as the metals used in combination with the stabilizing materials 30;70 because they have a magnetic field that is too strong and will change the trajectory of the element particles being emitted from an electronic device.

Element particles include photons, protons, quarks, electrons, etc. When electronic devices emit radiation (known as propagation of these element particles) this radiation has element particles with a disorganized spin. This disorganized spin is what is damaging to living organisms and electronic devices.

Materials that are ferromagnetic in their original state can organize the spin of these element particles, but in its original state they have too strong a magnetic field leading to a change in the whole trajectory of the radiation leading to signal loss, communication failures or failures of whatever function the electronic devices emitting this radiation is attempting to accomplish.

However, when a material is ferromagnetic in nanoscale and configured in the novel and non-obvious way subject of this invention, it can still organize the damaging disorganized spin of the element particles while not affecting the trajectory, and thus the function, of the radiation. The materials in powdered form 40;50 used having ferromagnetic properties in nanoscale should also be in a spontaneously stable ferromagnetic form when in nanoscale.

In addition, the materials used should be able to maintain their ferromagnetic properties when in nanoscale even while withstanding high Courie temperatures. For instance, gold, palladium, and titanium maintain their ferromagnetic properties in nanoscales up to a Courie temperature of approximately 544 degrees celsius. These materials need to be one that absorbs static. Organizing the polarization of the spins reduces static.

In a preferred embodiment, the ceramic powder 80 has a particle diameter of at least 150 nanometers. The ferromagnetic powder 60 a particle diameter of at least 100 nanometers. The remaining stabilizing material films 30;70 previously disclosed have a thickness of at least 1.5 microns. The thickness of the films or sheets are configured to the intended use. For larger applications, thicker layers of the stabilizing films are used. To apply the nanoscaled materials in powdered form to the films 30;70 the following methods can be used: electroplating, atomic layer deposition, or physical vapor deposition. The preferred method being the atomic layer deposition.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A tangible device having a surface comprising:

at least one waffler each created by making an indentation to said surface, a stabilizing film in each of said at least one waffler, a first nanoscale material having ferromagnetic properties when in nanoscale form, said first nanoscale material being applied to said at least one waffler on said surface of said device, said first nanoscale material being in powdered form and a predetermined amount of said first nanoscale material spread across said stabilizing film, said first nanoscale material being a metal, a ferromagnetic powder mixed with said first nanoscale material, a sealing agent material, said first nanoscale material and said ferromagnetic powder within said at least one waffler.

2. The apparatus of claim 1 wherein a plurality of wafflers are used within said tangible device.

3. The apparatus of claim 1 wherein a second nanoscale material is mixed with said first nanoscale material and said ferromagnetic material.

4. The apparatus of claim 3 wherein said first or said second nanoscale material is gold in powdered form.

5. The apparatus of claim 3 wherein said first or said second nanoscale material is palladium in powdered form.

6. The apparatus of claim 3 wherein said first nanoscale material or said second nanoscale material is titanium in powdered form.

7. The apparatus of claim 1 wherein said first nanoscale material has a particle diameter between 40 and 100 nanometers.

8. The apparatus of claim 7 wherein said first nanoscale material has a particle diameter of 97 nanometers.

* * * * *